United States Patent [19]

Takashima et al.

[11] Patent Number: 4,778,791

[45] Date of Patent: Oct. 18, 1988

[54] PHARMACEUTICAL COMPOSITION FOR IMPROVING CONSTITUTION OF LIPIDS IN BLOOD

[75] Inventors: Kohki Takashima, Tokyo; Tetsuji Mori, Yono; Taku Nagao, Tokyo, all of Japan

[73] Assignee: Tanabe Seiyaku Co., Ltd., Osaka, Japan

[21] Appl. No.: 46,889

[22] Filed: May 5, 1987

[30] Foreign Application Priority Data

May 16, 1986 [JP] Japan .................................. 61-113182

[51] Int. Cl.⁴ ............................................ A61K 31/55
[52] U.S. Cl. ...................................... 514/211; 514/824
[58] Field of Search ................. 514/211, 824; 540/491

[56] References Cited

U.S. PATENT DOCUMENTS 4,567,175  1/1986  Takeda et al. ...................... 514/211

Primary Examiner—Allen J. Robinson
Attorney, Agent, or Firm—Scully, Scott, Murphy & Presser

[57] ABSTRACT

Disclosed are a pharmaceutical composition for improving the constitution of lipids in blood, which comprises as an active ingredient 2-(4-methoxyphenyl)-3-acetoxy-5-[2-(dimethylamino)ethyl]-8-chloro-2,3-dihydro-1,5-benzothiazepin-4(5H)-one or a pharmaceutically acceptable acid addition salt thereof, use of the compound for preparing the pharmaceutical composition and a method of improving the constitution of lipids in blood.

5 Claims, No Drawings

PHARMACEUTICAL COMPOSITION FOR IMPROVING CONSTITUTION OF LIPIDS IN BLOOD

BACKGROUND OF THE INVENTION

This invention relates to a pharmaceutical composition for improving the constitution of lipids in blood, use of an 8-chlorobenzothiazepine compound for preparing the composition and a method of improving the constitution of lipids in blood by employing the same. Hyperlipidemia has been known as one of the causes for various adult diseases, and hypolipidemic agents such as clofibrate [chemical name: ethyl 2-(4-chlorophenoxy)-2-methylpropanoate], probucol [chemical name: 4,4'-{(1-methylethylidene)bis(thio)}bis{2,6-bis(1,1-dimethylethyl)phenol}], etc., have been used as curing and prophylactic agents therefor. Among hyperlipidemia, hypercholesterolemia has a strong causal relationship particularly to arteriosclerosis. On the other hand, cholesterol exists in blood in the forms of very low density lipoprotein (hereinafter called VLDL) cholesterol, low density lipoprotein (hereinafter called LDL) cholesterol, high density lipoprotein (hereinafter called HDL) cholesterol, etc., and among them VLDL and LDL promote deposition of cholesterol in the walls of arteries, but HDL prevents the deposition of cholesterol, as is known in the art [Annals of Internal Medicine, vol. 90, p. 85–91, 1979]. It has been also known that a negative correlation exists between HDL-cholesterol and incidence of ischemic heart disease, and that a person who has a high value of HDL-cholesterol will seldom suffer from ischemic heart disease (The Journal of Laboratory and Clinical Medicine, vol. 88, p. 941, 1976).

The present invention, in view of the state of the art as described above, provides a novel pharmaceutical composition for improving the constitution of lipids in blood, which is capable of increasing HDL-cholesterol quantity in blood.

SUMMARY OF THE INVENTION

More specifically, the present invention provides a pharmaceutical composition for improving the constitution of lipids in blood (hereinafter abbreviated merely as "the pharmaceutical composition of the present invention", which comprises as an active ingredient 2-(4-methoxyphenyl)-3-acetoxy-5-[2-(dimethylamino)ethyl]-8-chloro-2,3-dihydro-1,5-benzothiazepin-4(5H)-one (hereinafter abbreviated merely as "8-chlorobenzothiazepine compound") or a pharmaceutically acceptable acid addition salt thereof.

Further, the present invention provides a method of improving the constituion of lipids in blood.

Still further, the present invention provides use of the 8-chlorobenzothiazepine compound for preparing a pharmaceutical preparation for improving the constitution of lipids in blood.

DESCRIPTION OF THE PREFERRED EMBODIMENTS

The above 8-chlorobenzothiazepine compound or pharmaceutically acceptable acid addition salt thereof which is the active ingredient of the present invention itself is a useful pharmaceutical compound which has been known to have hypotensive activity and cerebral or coronary vasodilating activity (Japanese Unexamined patent publication No. 225174/1984 which corresponds to U.S. Pat. No. 4,567,175), but surprisingly, this compound exhibits the specific pharmacological effect that it increases remarkably only HDL-cholesterol quantity while maintaining or reducing VLDL- and LDL-cholesterol quantities in blood and additionally reduces serum triglyceride quantity, thus having excellent characteristics as an agent for improving the constitution of lipids in blood, i.e., for improving the lipoprotein composition ratio in blood (composition ratio of HDL-cholesterol relative to VLDL- and LDL-cholesterol). For example, when the (+)-cis-isomer of the 8-chlorobenzothiazepine compound (maleate) of the present invention is administered to SD-strain rats at a dose of 30 mg/Kg/day continuously for 7 days, the ratio of HDL-cholesterol quantity relative to total serum cholesterol quantity is increased by about 30% as compared with the group to which no test compound was administered.

The pharmaceutical composition of the present invention can be used by way of either oral administration or parenteral administration. In case of oral administration, the 8-chlorobenzothiazepine compound or a pharmaceutically acceptable acid addition salt thereof can be used as such or as a pharmaceutical preparation together with a pharmaceutical carrier suitable for oral administration such as excipient, binder, disintegrator, lubricant, etc. As the pharmaceutical carriers described above, for example, conventional excipients, binders, disintegrators, lubricants such as starch, lactose, glucose, gelatin, sorbitol, tragacanth gum, polyvinylpyrrolidone, sugar, corn starch, polyethylene glycol, talc, potassium phosphate, magnesium stearate and others can suitably be used. Also, the dosage form may be a solid preparation such as tablets, pills, capsules, suppositories or it may also be a liquid preparation such as solutions, suspensions, emulsions. On the other hand, in case of parenteral administration, the pharmaceutical composition of the present invention may be preferably used as an injection preparation, and as the pharmaceutical carrier for this purpose, for example, distilled water for injection, vegetable oil, propylene glycol, etc., can be suitably used, and further dissolving aids, buffering agent, stabilizing agent, etc., may be also contained.

The 8-chlorobenzothiazepine compound which is the active ingredient of the present invention can be used as a free base or as a pharmaceutically acceptable acid addition salt thereof. Examples of pharmaceutically acceptable acid addition salt may include inorganic acid addition salts such as hydrochloride, hydrobromide, hydroiodide, perchlorate, sulfate, phosphate; or organic acid addition salts such as oxalate, maleate, fumarate, tartarate, methanesulfonate and the like.

The dose of the pharmaceutical composition of the present invention may differ depending on the kind of disease, the age and body weight of the patient, the severity of disease and the route of administration, but the dose of the 8-chlorobenzothiazepine compound or a pharmaceutically acceptable acid addition salt thereof which is the active ingredient should be generally 3 to 500 mg, preferably 5 to 100 mg, per day for human adult, in case of oral administration.

Since the 8-chlorobenzothiazepine compound which is the active ingredient of the present invention has two asymmetric carbon atoms in the molecule, there exist two kinds of stereoisomers (namely, cis- and trans-isomers) or four kinds of optical isomers (namely, (+)-cis-, (−)-cis-, (+)-trans- and (−)-trans-isomers). For the object of the present invention, all of these isomers and mixtures thereof can be used, but it is generally preferable to use a cis-isomer.

As described above, the pharmaceutical composition of the present invention containing the 8-chlorobenzothiazepine compound or a pharmaceutically acceptable acid addition salt as the active ingredient has the effect of improving the lipid constitution in blood, for example, the effect of increasing HDL-cholesterol quantity in blood while maintaining or reducing VLDL- and LDL-cholesterol quantities in blood and further reducing serum triglyceride quantity, etc., and therefore it can be effectively used as a prophylactic and curing agent of various diseases caused by increase of lipids in blood such as cholesterol, etc.

EXAMPLES

Experimental example 1

SD-strain male rats (one group: 8 rats, averagebody weight: 135 g) were fed ad libitum with a diet containing 2 w/w% of cholesterol and 0.5 w/w% of sodium cholate [CE-2; produced by Nihon CLEA], and (+)-cis-8-chlorobenzothiazepine compound (maleate) (suspended in 10 ml of distilled water) was orally administered by stomach tube for 7 days at a dose of 30 mg or 60 mg/Kg/day. On the other hand, in the control group, rats were fed ad libitum with the above diet containing cholesterol and sodium cholate. After administration, blood was collected from the abdominal aorta under ether anesthesia, and the amount of cholesterol in serum obtained by centrifugation of said blood was assayed according to an enzymatic method (Clinical Chemistry, vol. 20, p. 470, 1974). Also, from a part of said serum, serum HDL was separated according to the lipoprotein precipitation method by use of sodium dextran sulfate (Canadian Journal of Biochemistry, vol. 47, p. 1043, 1969) and HDL-cholesterol quantity was assayed according to the above enzymatic method. The serum triglyceride quantity was assayed according to an enzymatic method [Rinsho Kensa (Clinical Test), vol. 22, p. 1304, 1978].

(Results)
The results are shown in Table 1.

TABLE 1

| | Test compound administration group (dose; mg/Kg/day) | | Control group |
|---|---|---|---|
| | 30 | 60 | |
| Serum cholesterol quantity (mg/dl) | 195.4 | 199.6 | 193.1 |
| HDL-cholesterol quantity (mg/dl) [Increase ratio[a] (%)] | 20.4 [22.9] | 20.6 [24.1] | 16.6 |
| Serum triglyceride quantity (mg/dl) [Decrease ratio[b] (%)] | 84.3 [16.0] | 84.1 [16.2] | 100.4 |

[a]"Increase ratio" means the percentage of the amount increased of HDL-cholesterol quantity between the test compound administration group and control group.
[b]"Decrease ratio" means the percentage of the amount decreased of serum triglyceride quantity between the test compound administration group and control group.

Experimental example 2

(+)-Cis-8-chlorobenzothiazepine compound (maleate) (dissolved in 5 ml of distilled water) was orally administered to SHR-strain male rats (age: 21 weeks, test compound administration group: 11 rats, control group: 13 rats) for 28 days at a dose of 30 or 60 mg/Kg/day. On the other hand, distilled water was administered to the control group at a dose of 5 ml/Kg/day. After administration, blood was collected from the abdominal aorta under ether anesthesia, and said blood was treated in the same manner as described in Experimental example 1 to determine serum cholesterol quantity and HDL-cholesterol quantity. Based on these results, the lipoprotein composition ratio in blood was calculated from the following formula.

$$\text{Lipoprotein composition ratio in blood} = \frac{\text{HDL-cholesterol quantity}}{\text{Serum cholesterol quantity} - \text{HDL-cholesterol quantity}}$$

(Results)
The results are shown in Table 2.

TABLE 2

| | Test compound administration group (dose; mg/Kg/day) | | Control group |
|---|---|---|---|
| | 30 | 60 | |
| Serum cholesterol quantity (mg/dl) | 68.6 | 75.7 | 57.8 |
| HDL-cholesterol quantity (mg/dl) | 48.6 | 57.4 | 36.6 |
| Lipoprotein composition ratio in blood [Amelioration ratio[c] (%)] | 2.48 [37.8] | 3.44 [91.1] | 1.80 |

[c]"Amelioration ratio" means the percentage of the lipoprotein composition ratio increased between the test compound administration group and control group.

Experimental example 3

SD-strain male rats (one group: 5 rats, average body weight: about 120 g) were fed ad libitum for 7 days with a diet containing 0.2 w/w % of (+)-cis-8-chlorobenzothiazepine compound (maleate), 2 w/w % of cholesterol and 0.5 w/w % of sodium cholate. On the other hand, the control group was fed ad libitum with the diet containing cholesterol and sodium cholate only. After administration, blood was collected from the abdominal aorta under ether anesthesia, and said blood was treated in the same manner as described in Experimental example 1 to determine serum cholesterol quantity and HDL-cholesterol quantity.

(Results)
The results are shown in Table 3.

TABLE 3

| | Test compound administration group | Control group |
|---|---|---|
| Serum cholesterol quantity (mg/dl) | 194.5 | 181.3 |
| HDL-cholesterol quantity (mg/dl) [Increase ratio[a] (%)] | 34.2 [52.7] | 20.4 |

[a]The same as the note of Table 1.

Example 1

(Tablet)

| | |
|---|---|
| (+)-Cis-8-chloro-benzothiazepine compound (maleate) | 45.0 g |
| Corn starch | 20.1 g |
| Lactose | 82.4 g |
| Polyvinylpyrrolidone | 3.0 g |
| Crystalline cellulose | 38.0 g |
| Magnesium stearate | 1.5 g |
| Total | 190.0 g |

The (+)-cis-8-chlorobenzothiazepine compound (maleate), lactose and corn starch were mixed with an alcohol solution of polyvinylpyrrolidone and granulated by kneading according to the wet granulation method, followed by drying to be formed into granules. Subsequently, magnesium stearate and crystalline cellulose were added to the granules and the mixture is compressed by a tabletting machine to give tablets of 8 mm in diameter and 190 mg in weight.

Example 2

(Injection)

Ten grams of (+)-Cis-8-chlorobenzothiazepine compound (maleate) were dissolved in 2 liter of distilled water for injection. The solution was filtered through a membrane filter with a pore size of 0.22 μm, and was poured into ampoules under aseptic conditions each in 2 ml and sealed to give ampoules for injection.

Example 3

(Powders)

| | |
|---|---|
| (+)-Cis-8-chlorobenzothiazepine compound (maleate) | 10 g |
| Lactose | 90 g |
| Total | 100 g |

The above-mentioned ingredients were homogeneously mixed in a double conical mixer to give 10-fold trituration.

We claim:

1. A method for increasing the ratio of HDL-cholesterol quantity to total serum cholesterol quantity in a human being in need thereof, which comprises administering to said human being a pharmaceutically effective amount of 2-(4-methoxyphenyl)-3-acetoxy-5-[2-(dimethylamino)ethyl]-8-chloro-2,3-dihydro-1,5-benzothiazepin-4(5H)-one or a pharmaceutically acceptable acid addition salt thereof.

2. The method according to claim 1, wherein the compound to be administered is (+)-cis-2-(4-methoxyphenyl)-3-acetoxy-5-[2-(dimethylamino)ethyl]-8-chloro-2,3-dihydro-1,5-benzothiazepin-4(5H)-one or a pharmaceutically acceptable acid addition salt thereof.

3. The method according to claim 2 wherein said pharmaceutically acceptable acid addition salt is selected from the group consisting of hydrochloride, hydrobromide, hydroiodide, perchlorate, sulfate, phosphate oxalate, maleate, fumarate, tartarate and methanesulfonate.

4. The method according to claim 2, wherein said pharmaceutically acceptable acid addition salt is maleate.

5. The method according to claim 2, wherein said pharmaceutically effective amount of the compound is 3 to 500 mg/day.

* * * * *